US006531424B2

(12) United States Patent
Ittel et al.

(10) Patent No.: US 6,531,424 B2
(45) Date of Patent: Mar. 11, 2003

(54) POLYMERIZATION OF OLEFINS

(75) Inventors: Steven Dale Ittel, Wilmington, DE (US); Ying Wang, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/735,560

(22) Filed: Dec. 13, 2000

(65) Prior Publication Data

US 2002/0107345 A1 Aug. 8, 2002

Related U.S. Application Data

(60) Provisional application No. 60/172,261, filed on Dec. 17, 1999.

(51) Int. Cl.$^7$ .......................... B01J 31/28; B01J 31/38; C08F 4/44

(52) U.S. Cl. ...................... 502/155; 502/167; 526/161; 526/171; 526/172; 556/32; 556/35; 564/270; 564/271

(58) Field of Search ................................ 502/117, 155, 502/167, 162; 526/161, 171, 172; 556/32, 35; 564/270, 271

(56) References Cited

U.S. PATENT DOCUMENTS

| 3,661,898 A | 5/1972 | Dehnert et al. |
| 3,933,785 A | 1/1976 | Back et al. |
| 5,714,556 A | 2/1998 | Johnson et al. |
| 5,880,241 A | 3/1999 | Brookhart et al. |
| 6,060,569 A | 5/2000 | Bennett et al. |

FOREIGN PATENT DOCUMENTS

| DK | 99 556 | 8/1973 | |
| EP | 0 874 005 A1 | * 10/1998 | |
| FR | 2013609 | 3/1970 | |
| WO | WO 98/30609 | 7/1998 | |
| WO | WO 98/42664 | 10/1998 | |
| WO | WO 98/42665 | 10/1998 | |

OTHER PUBLICATIONS

Beringhelli et al., Gazzeta Chimica Italiana 115, 1985, pp. 181–186.*
Tisato et al., J. Chem. Soc. Dalton Trans. 1990, pp. 2225–2232.*
Dahl et al., ACTA Chemica Scandinavica 23 (1969) pp. 1503–1513.*
Wang, Z. et al., Desugn, Synthesis, and X–ray Structural Characterization of Nw Dinucleating Macrocyclic Ligands and a Novel Phenolate–Bridged Dilanthanum(III) Complex, Inorg. Chem., 1997, 629–636, 36(4).
Rao, Chevrolu P. et al., Oxo–metal complexes of alkoxo rich ligands of vanadium complexes, Proc. Indian Acad. Sci. (Chem. Sci.), 1999, 479–187, 111(3).

Rath, Sankar Prasad et al., Synthesis, Structure and Catecholase Reaction of a Vanadate Ester System Incorporating Monoionized Catechol Chelation, Inorg. Chem., 1999, 4376–4377, 38(20).
Ligtenbarg, Alette G. J. et al., Vanadium(v) complexes based on a bis(pyridine)–imine ligand (HL); synthesis and crystal structure of a dioxivanadium(v) complex involving a ligand cyclisation, J. Chem. Soc., Dalton Trans., 1999, 659–661, 5.
Asgedom, Gebray et al., Monooxovanadium(v) mixed ligand complexes of schiff bases and catecholates: synthesis, spectral and electrochemical characterization, Polyhedron, 1996, 3731–3739, 15(21).
Asgedom, Gebray et al., Structure, characterization and photoreativity of monomeric dioxovanadium(v) Schiff–base complexes of trigonal–bipyramidal geometry, J. Chem. Soc., Dalton Trans., 1996, 93–97, 1.
Abramenko, V.L. et al., Molybdenyl complexes with o–hydroxyazomethines, Database Chemabs [Online], Koorrd. Khim, 1985, 918–927, 11(7).
Frederick, F. C. et al., Electrochemistry and Oxygenation Kinects of Tridentate Schiff Base Manganese Complexes, Inorg. Chem., 1983, 792–795, 22(5).
Tisato Francesco et al., Synthesis and Characterization of Technetium(v) and Rhenium(v) Oxo complexes with Schiff–base ligands containing the ONN Donor–atom Set. Molecular Structure of trans–Dichloro–oxo[1–(8'–quinolyliminomethyl)–2–naphtholato–NN'O]technetium(v), J. Chem. Soc., Dalton Trans., 1990, 2225–2228, 7.
Esmadi, Fatima T. et al., Double bond transfer in 2–hydroxyl–1–naphthalidine–8–aminoquinoline and some of its nickel(II) complexes, Canadian Journal of Analytical Sciences and Spectroscopy, 1999, 114–118, 44(4).
Viswanathan, Rathinam et al., Analogues of the iron–binding site in catechol 1,2–dioxygenase: iron(III) complexes of benzimidazole–and pyridine–containing tridentate ligands, J. Chem. Soc., Dalton Trans., 1995, 1259–1260,8.
Donia, Ahmed M. et al., Reversible and irreversible thermochromism of some Schiff base metal complexes, Transition Met. Chem., 1993, 315–318, 18(3).
Chen, Dian et al., New synthetic cobalt schiff base complexes as oxygen carriers, Inorg. Chem., 1989, 2647–2652, 28(13).
Brunner, Henri et al., Asymmetric catalysis. XXXVII. Complexes with free donor groups as co–catalysts for enantioselective hydrosilylation, J. Organomet. Chem., 1987, 15–27, 335(1).

(List continued on next page.)

Primary Examiner—David W. Wu
Assistant Examiner—R. Harlan

(57) ABSTRACT

Olefins, such as ethylene, are polymerized using as a polymerization catalyst a complex of a selected transition metal with a monoanionic ligand that has at least three atoms that may coordinate to the transition metal. Also disclosed are the above selected transition metal complexes, and intermediates thereto.

7 Claims, No Drawings

OTHER PUBLICATIONS

Oshio, Hiroki et al., New spin–crossover iron(III) complexes with free large hysteresis effects and time dependence of their magnetism, J. Chem. Soc. Dalton Trans., 1987, 1341–1347, 6.

Beringhelli, Tiziana et al., Spectroscopic and spectroscopic properties of cobalt(II) bis derivatives with tridentate schiff bases and their adducts with molecular oxygen, Gazzetta Chimica Italiana, 1985, 181–186, 115(3).

Maeda, Yonezo et al. Examples of fast and slow electronic relaxation between $^6A$ and $^2T$, Inorg. Chem., 1984, 2440–2447, 23(16).

Beringhelli, Tiziana et al., Different routes of electron transfer to oxygen, in polydentate Schiff base cobalt(II) complexes, Database Chemabs [Online], Congr. Naz. Chim. Inorg., [ATTI], 15th, 1982, 233–236, Soc. Chim. Ital. Div. Chim. Inorg., Bari, Italy.

Beringhelli, Tiziana et al., Polydentate Schiff–base cobalt(II) complexes: solid state and solution behavior, Database Chemabs [Online], Congr. Naz. Chim. Inorg., [ATTI], 16th, 1983, 361–362, Univ. Studi Ferrara, Ferrara, Italy.

Dickinson, Richard C. et al., The magnetic properties of bis[n–(8–quinoly)–salicylaldimine]halogenoiron(III).x hydrate, Fe(*–Qs)$_2$X$_x$H$_2$O: a reaxamination, J. Inorg. Nucl. Chem., 1977, 1531, 39(9).

Dahl, Britta M. et al., Studies of Chelates with heterocyclic ligands IV. Transition metal complexes with N–(8–Quinoly)salicylaldimine, ACTA Chemica Scandinavica, 1969, 1503–1513, 23(5).

Esmadi, Fatima T. et al., Reaction of some schiff base complexes of iron(III) with nitrogen and sulfur donor anions, Synth. React. Inorg. Met.–Org. Chem., 2000, 1347–1362, 30(7).

* cited by examiner

POLYMERIZATION OF OLEFINS

CROSS-REFERENCE TO RELATED APPLICATION

This application claims priority under 35 U.S.C. §119 from U.S. Provisional Application Ser. No. 60/172,261 (filed Dec. 17, 1999), which is incorporated by reference herein for all purposes as if fully set forth.

FIELD OF THE INVENTION

Olefins, such as ethylene, are polymerized using as a polymerization catalyst a complex of a selected transition metal with a monoanionic ligand that has three donor atoms which may coordinate to the transition metal.

TECHNICAL BACKGROUND

Polymers of olefins are important items of commerce, and these polymers are used in a myriad of ways, from low molecular weight polyolefins being used as a lubricant and in waxes, to higher molecular weight grades being used for fiber, films, molding resins, elastomers, etc.

Olefins may be polymerized by a variety of transition metal containing catalysts, for example metallocene and Ziegler-Natta type catalysts. More recently, late transition metal containing polymerization catalysts have also been discovered, and among them are nickel and other transition metal containing catalysts in which the nickel atom is complexed to a neutral or monoanionic ligand, see for instance U.S. Pat. No. 5,714,556, U.S. Pat. No. 5,880,241, U.S. Pat. No. 6,060,569, WO9842664, WO9842665 and WO9830609, all of which are incorporated by reference herein for all purposes as if fully set forth. None of these references describes the complexes disclosed herein. Since polyolefins are important commercial materials, new catalysts for their manufacture are constantly being sought.

SUMMARY OF THE INVENTION

One aspect of the present invention concerns a first process for the polymerization of olefins, comprising the step of contacting, at a temperature of about −100° C. to about +200° C., one or more monomers selected from the group consisting of ethylene and an olefin of the formula $H_2C=CH(CH_2)_nG$ (XVII), with an active catalyst comprising a Group 3 to Group 10 transition metal complex of an anion of the formula (I)

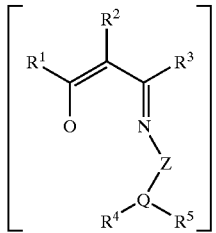

(I)

wherein:

$R^1$ is hydrocarbyl or substituted hydrocarbyl, and $R^2$ is hydrogen, hydrocarbyl or substituted hydrocarbyl, and provided that $R^1$ and $R^2$ taken together may be ortho-arylene or substituted ortho-arylene;

$R^3$ is hydrogen, hydrocarbyl, substituted hydrocarbyl or a functional group, provided that when $R^1$ and $R^2$ taken together are ortho-arylene or substituted ortho-arylene, $R^3$ may form a fused ring system therewith;

Q is nitrogen, oxygen, phosphorous or sulfur;

$R^4$ and $R^5$ are each independently hydrogen, hydrocarbyl, or substituted hydrocarbyl, provided that $R^4$ and $R^5$ taken together may form a ring, and further provided that when Q is oxygen or sulfur $R^5$ is not present;

Z is a bridging group of the formula (II) or (III)

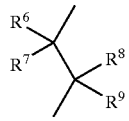

(II)

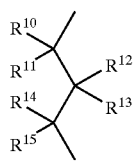

(III)

$R^6$ is hydrogen, hydrocarbyl or substituted hydrocarbyl, provided that $R^3$ and $R^6$ together may form a ring;

$R^7$ is hydrogen, hydrocarbyl or substituted hydrocarbyl, provided that $R^3$, $R^6$ and $R^7$ together may form an aromatic ring or $R^6$ and $R^7$ taken together may form a ring;

$R^8$ is hydrogen, hydrocarbyl or substituted hydrocarbyl;

$R^9$ is hydrogen, hydrocarbyl or substituted hydrocarbyl, provided that $R^4$ and $R^9$ taken together may be part of a double bond to an imino nitrogen atom, or $R^8$ and $R^9$ taken together may form a ring, or $R^4$, $R^5$, $R^8$ and $R^9$ taken together may form an aromatic ring, or $R^4$ and $R^9$ taken together may form a ring, or $R^4$, $R^8$ and $R^9$ taken together may form a ring, or $R^4$, $R^5$, $R^6$, $R^7$, $R^8$, and $R^9$ taken together may form a fused aromatic ring system;

$R^{10}$, $R^{11}$, $R^{12}$ and $R^{13}$ are each independently hydrogen, hydrocarbyl or substituted hydrocarbyl or $R^{10}$, $R^{11}$, $R^{12}$ and $R^{13}$ taken together are ortho-arylene;

$R^{14}$ is hydrogen, hydrocarbyl or substituted hydrocarbyl;

$R^4$ and $R^{15}$ together are part of a double bond to an imino nitrogen atom;

n is an integer of 1 or more;

G is hydrogen, $-CO_2R^{16}$ or $-C(O)NR^{16}_2$; and each $R^{16}$ is independently hydrogen, hydrocarbyl or substituted hydrocarbyl.

Another aspect of the present invention conerns a second process for the polymerization of olefins, comprising the step of contacting, at a temperature of about −100° C. to about +200° C., one or more monomers selected from the group consisting of ethylene and $H_2C=CH(CH_2)_nG$ (XVII), with a compound of the formula (IV)

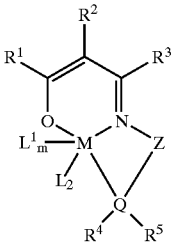

(IV)

wherein:

$R^1$ is hydrocarbyl or substituted hydrocarbyl, and $R^2$ is hydrogen, hydrocarbyl or substituted hydrocarbyl, and provided that $R^1$ and $R^2$ taken together may be ortho-arylene or substituted ortho-arylene;

$R^3$ is hydrogen, hydrocarbyl, substituted hydrocarbyl or a functional group, provided that when $R^1$ and $R^2$ taken together are ortho-arylene or substituted ortho-arylene, $R^3$ may form a fused ring system therewith;

$R^4$ and $R^5$ are each independently hydrogen, hydrocarbyl, or substituted hydrocarbyl, provided that $R^4$ and $R^5$ taken together may form a ring, and further provided that when Q is oxygen or sulfur $R^5$ is not present;

Q is nitrogen, oxygen, phosphorous or sulfur;

Z is a bridging group of the formula (II) or (III)

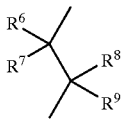
(II)

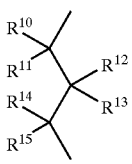
(III)

$R^6$ is hydrogen, hydrocarbyl or substituted hydrocarbyl, or $R^3$ and $R^6$ together may form a ring;

$R^7$ is hydrogen, hydrocarbyl or substituted hydrocarbyl, provided that $R^3$, $R^6$ and $R^7$ together may form an aromatic ring, or $R^6$ and $R^7$ taken together may form a ring;

$R^8$ is hydrogen, hydrocarbyl or substituted hydrocarbyl;

$R^9$ is hydrogen, hydrocarbyl, substituted hydrocarbyl, or $R^4$ and $R^9$ taken together may be part of a double bond to an imino nitrogen atom, or $R^8$ and $R^9$ taken together may form a ring, or $R^4$, $R^5$, $R^8$ and $R^9$ taken together may form an aromatic ring, or $R^4$ and $R^9$ taken together may form a ring, or $R^4$, $R^8$ and $R^9$ taken together may form a ring, or $R^4$, $R^5$, $R^6$, $R^7$, $R^8$ and $R^9$ taken together may form a fused aromatic ring system;

$R^{10}$, $R^{11}$, $R^{12}$ and $R^{13}$ are each independently hydrogen, hydrocarbyl or substituted hydrocarbyl, or $R^{10}$, $R^{11}$, $R^{12}$ and $R^{13}$ taken together are ortho-arylene;

$R^{14}$ is hydrogen, hydrocarbyl or substituted hydrocarbyl;

$R^4$ and $R^{15}$ together are part of a double bond to an imino nitrogen atom;

n is an integer of 1 or more;

G is hydrogen, —$CO_2R^{16}$, or —$C(O)NR^{16}{}_2$;

each $R^{16}$ is independently hydrogen, hydrocarbyl, or substituted hydrocarbyl;

M is a Group 3 to Group 10 transition metal;

m is an integer equal to the valence of M minus 1; and each $L^1$ is independently a monodentate monoanionic ligand and at least for one of $L^1$ an ethylene molecule may insert between $L^1$ and M, and $L^2$ is a monodentate neutral ligand which may be displaced by ethylene or an empty coordination site, or an $L^1$ and $L^2$ taken together are a monoanionic polydentate ligand and at least for one of these polydentate ligands ethylene may insert between said monoanionic polydentate ligand and M.

In the above-mentioned processes, (IV) and/or the transition metal complex of (I) may in and of themselves be active catalysts, or may be "activated" by contact with a co-catalyst/activator.

The present invention also concerns a compound of the formula (V)

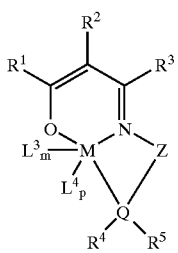
(V)

wherein $R^1$, $R^2$, $R^3$, $R^4$, $R^5$, Q, Z (and all R groups associated with Z), M and m are as defined above for (IV), p is 0 or 1; and each $L^3$ is independently a monodentate monoanionic ligand, and $L^4$ is a monodentate neutral ligand or an empty coordination site, or an $L^3$ and $L^4$ taken together are a monoanionic bidentate ligand.

Further aspects of the present invention include, for example, the anion of the formula (I) as defined above, as well as a Group 3 to Group 10 transition metal complex of such anion.

DETAILED DESCRIPTION OF THE PREFERRED EMBODIMENTS

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups herein contain 1 to about 30 carbon atoms.

By "substituted hydrocarbyl", herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{22}$ wherein $R^{22}$ is hydrocarbyl or substituted hydrocarbyl. In cases in which the functional group may be near a metal atom the functional group should not coordinate to the metal atom more strongly than the groups in those compounds are shown as coordinating to the metal atom, that is they should not displace the desired coordinating group.

By a "catalyst activator" is meant a compound that reacts with a transition metal compound to form an activated catalyst species. A preferred catalyst activator is an "alkyl aluminum compound", that is, a compound which has at least one alkyl group bound to an aluminum atom. Other groups such as alkoxide, hydride, and halogen may also be bound to aluminum atoms in the compound.

By "neutral Lewis base" is meant a compound, which is not an ion, that can act as a Lewis base. Examples of such compounds include ethers, amines, sulfides and organic nitriles.

By "neutral Lewis acid" is meant a compound, which is not an ion, that can act as a Lewis acid. Examples of such compounds include boranes, alkylaluminum compounds, aluminum halides and antimony [V] halides.

By "cationic Lewis acid" is meant a cation that can act as a Lewis acid. Examples of such cations are sodium and silver cations.

By an "empty coordination site" is meant a potential coordination site on a metal atom that does not have a ligand bound to it. Thus if an ethylene molecule is in the proximity of the empty coordination site, the ethylene molecule may coordinate to the metal atom.

By a "ligand into which an ethylene molecule may insert" between the ligand and a metal atom is meant a ligand coordinated to the metal atom into which an ethylene molecule (or a coordinated ethylene molecule) may insert to start or continue a polymerization. For instance, this may take the form of the reaction (wherein L is a ligand):

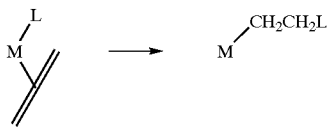

By a "ligand which may be displaced by ethylene" is meant a ligand coordinated to a transition metal, which when exposed to ethylene is displaced as the ligand by the ethylene.

By a "monoanionic ligand" is meant a ligand with one negative charge.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By a "π-allyl group" is meant a monoanionic ligand with 1 $sp^3$ and two adjacent $sp^2$ carbon atoms bound to a metal center in a delocalized $\eta^3$ fashion. The three carbon atoms may be substituted with other hydrocarbyl groups or functional groups.

By "ortho-arylene" (or "o-arylene") is meant a divalent aryl group in which the free valencies are on adjacent carbon atoms. The o-arylene ring may be part of a fused and/or heterocyclic ring system and/or contain substituents such as hydrocarbyl groups or functional groups.

The polymerizations herein are carried out by a transition metal complex of anion (I). Many of the groups in (I) may have various forms, that is they may be "simple" groups such as hydrogen or alkyl, or they may participate in multiple bonds such as an imino bond to nitrogen or a carbon atom in an aromatic ring and/or they may be part of ring or ring systems. Some of these groups may optionally for instance be part of two different rings. Clearly simple valence rules are not broken in these anions and compounds, for example carbon will have a valence of 4. Thus if a particular group is part of one ring, it cannot be part of another ring or group that would violate these simple valence rules.

In order to illustrate this, and since (I) and its conjugate acid and transition metal complexes may have various individual structures, some conjugate acids of these anions are shown below, with some salient features pointed out.

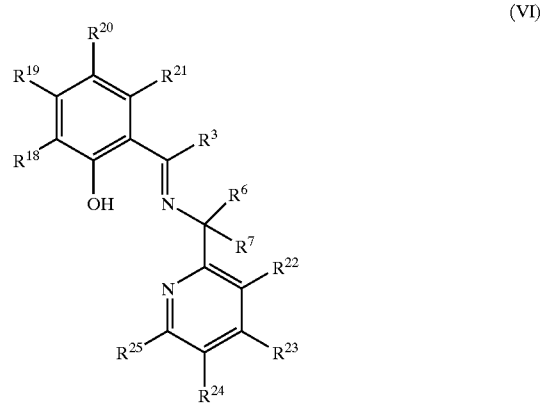

(VI)

In (VI), $R^1$ and $R^2$ taken together are o-arylene; Z is a bridging group of the formula (II); and $R^4$, $R^5$, $R^8$ and $R^9$ taken together form an aromatic ring. In addition, each of $R^{18}$, $R^{19}$, $R^{20}$, $R^{21}$, $R^{22}$, $R^{23}$, $R^{24}$ and $R^{25}$ is independently, hydrogen, hydrocarbyl, substituted hydrocarbyl or a functional group, provided that any two of $R^{18}$, $R^{19}$, $R^{20}$ and $R^{21}$ vicinal to one another may form a ring, any two of $R^{22}$, $R^{23}$, $R^{24}$ and $R^{25}$ vicinal to one another may form a ring, and $R^3$ and $R^{21}$ taken together may form a ring.

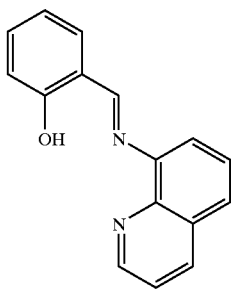

(VII)

In (VII), R¹ and R² taken together are o-arylene; Z is a bridging group of the formula (II); R³ is hydrogen; and R⁴, R⁵, R⁶, R⁷, R⁸ and R⁹ form a fused aromatic ring system.

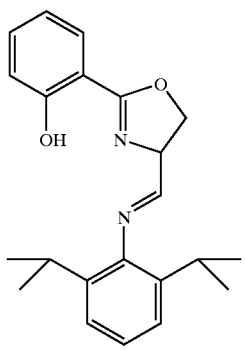

(VIII)

In (VIII), R¹ and R² taken together are o-arylene; Z is a bridging group of the formula (II); R³ and R⁶ taken together form a ring; R⁷ and R⁸ are hydrogen; R⁴ and R⁹ taken together form part of an imino bond to nitrogen; and R⁵ is 2,6-diisopropylphenyl.

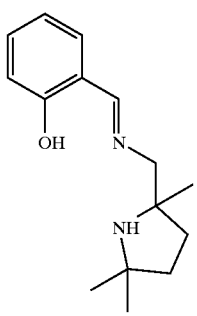

(IX)

In (IX), R¹ and R² taken together are o-arylene; Z is a group of the formula (II); R³ is hydrogen; R⁵, R⁶ and R⁷ are hydrogen, and R⁴ and R⁹ taken together form a ring.

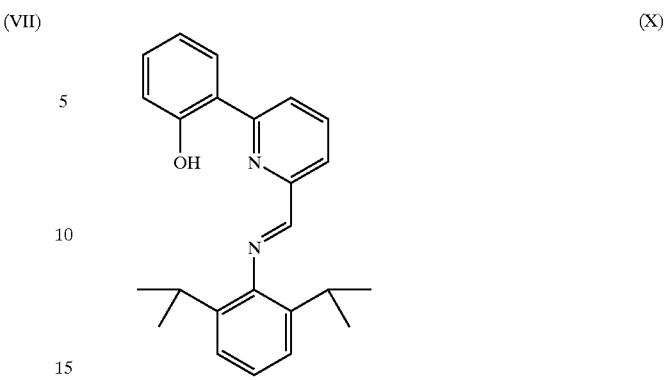

(X)

In (X), R¹ and R² taken together are o-arylene; Z is a group of the formula (II); R³, R⁶ and R⁷ together form an aromatic ring; R⁴ and R⁹ taken together form part of an imino bond to nitrogen; R⁸ is hydrogen; and R⁵ is 2,6-diisopropylphenyl.

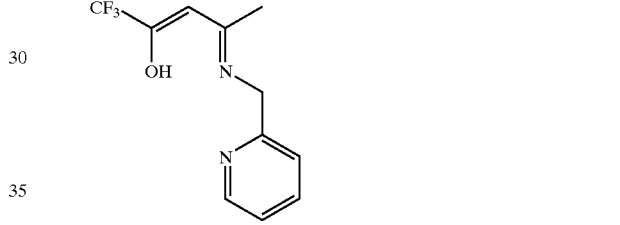

(XI)

In (XI), R¹ is trifluoromethyl; Z is a group of the formula (II); R⁴, R⁶, and R⁷ are hydrogen; R³ is methyl; and R⁴, R⁵, R⁸ and R⁹ taken together form an aromatic ring.

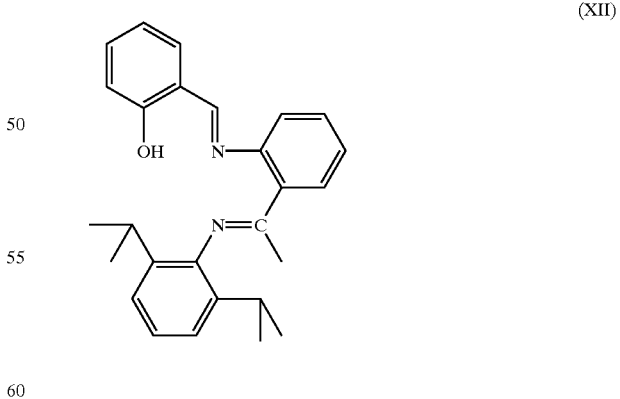

(XII)

In (XII), R¹ and R² taken together are o-arylene; R³ is hydrogen; Z is a group of the formula (III); R¹⁰, R¹¹, R¹² and R¹³ taken together are o-arylene; R¹⁴ is methyl; R⁴ and R¹⁵ together are part of a double bond to an imino nitrogen atom; and R⁵ is 2,6-diisopropylphenyl.

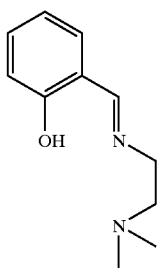
(XIII)

In (XIII), $R^1$ and $R^2$ taken together are o-arylene; $R^3$ is hydrogen; Z is a group of the formula (II); $R^6$, $R^7$, $R^8$ and $R^9$ are hydrogen; and $R^4$ and $R^5$ are methyl.

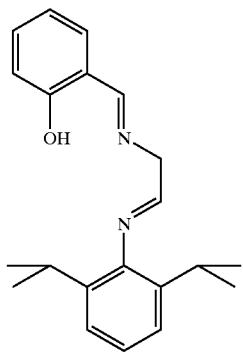
(XIV)

In (XIV), $R^1$ and $R^2$ taken together are o-arylene; Z is a group of the formula (II); $R^3$, $R^6$, $R^7$ and $R^8$ are hydrogen; $R^4$ and $R^9$ together are part of a double bond to an imino nitrogen atom; and $R^5$ is 2,6-diisopropylphenyl.

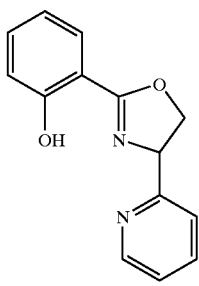
(XV)

In (XV), $R^1$ and $R^2$ taken together are o-arylene; Z is a bridging group of the formula (II); $R^3$ and $R^6$ taken together form a ring; $R^7$ is hydrogen; and $R^4$, $R^5$, $R^8$ and $R^9$ taken together form an aromatic ring.

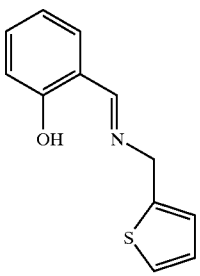
(XVIII)

In (XVIII), $R^1$ and $R^2$ taken together are o-arylene; Z is a group of the formula (II); $R^3$, $R^6$ and $R^7$ are hydrogen; Q is sulfur and thus $R^5$ is not present; and $R^4$, $R^8$ and $R^9$ together form a ring.

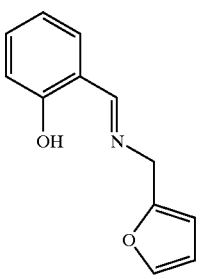
(XIX)

In (XIX), $R^1$ and $R^2$ taken together are o-arylene; Z is a group of the formula (II); $R^3$, $R^6$ and $R^7$ are hydrogen; Q is oxygen and thus $R^5$ is not present; and $R^4$, $R^8$ and $R^9$ together form a ring.

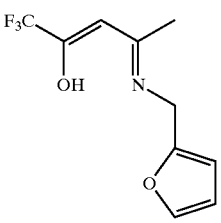
(XX)

In (XX), $R^1$ is trifluoromethyl; $R^2$ is hydrogen; $R^3$ is methyl; Z is a group of the formula (II); $R^6$ and $R^7$ are hydrogen; Q is oxygen and thus $R^5$ is not present; and $R^4$, $R^8$ and $R^9$ together form a ring.

In all of compounds (VI) through (XV) and (XVIII) through (XX), groups and/or substituents may be changed where appropriate, for example methyl groups may be changed to other hydrocarbyl groups or hydrogen, hydrogen may be change to hydrocarbyl or functional groups.

A preferred anion (and it conjugate acid and metal complexes) is (VI). In (VI) it is preferred that:

$R^{18}$ and $R^{21}$ are each independently alkyl containing 1 to 4 carbon atoms, halo, nitro or hydrogen; and/or $R^{19}$ and $R^{20}$ are hydrogen;

$R^3$ is hydrogen; and/or $R^6$ and $R^7$ are hydrogen; and/or $R^{22}$, $R^{23}$, $R^{24}$ and $R^{25}$ are hydrogen; and/or Q is nitrogen.

In preferred specific compounds (VI), $R^{18}$ and $R^{21}$ are both nitro or t-butyl, and $R^{19}$, $R^{20}$, $R^3$, $R^6$, $R^7$, $R^{22}$, $R^{23}$, $R^{24}$ and $R^{25}$ are hydrogen; $R^{18}$, $R^{21}$, $R^{19}$, $R^{20}$, $R^3$, $R^6$, $R^7$, $R^{22}$, $R^{23}$, $R^{24}$ and $R^{25}$ are all hydrogen; $R^{18}$ is t-butyl and $R^{19}$, $R^{20}$, $R^{21}$, $R^3$, $R^6$, $R^7$, $R^{22}$, $R^{23}$, $R^{24}$ and $R^{25}$ are hydrogen.

The structure illustrated in (I) is not meant to preclude other tautomers, and all such tautomers are included herein. For instance such structures may include

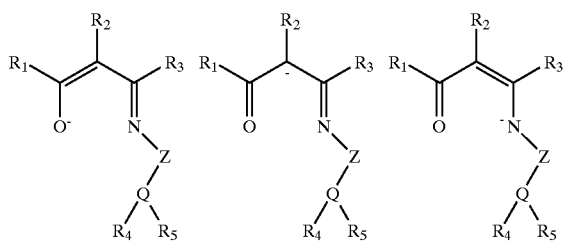

The conjugate acids of (I) can be made by a variety of methods, most of which are familiar to the skilled organic synthetic chemist, and which method(s) are chosen will depend on the particular structure desired, such as (VI) through (XV). In all instances, if certain substituents/ substitution patterns are desired, starting materials with those substituents/substitution patterns may be used. For example (VI) may be made by reacting an appropriate salicylaldehyde with an appropriate 2-aminomethylpyridine. (VII) may be made by reacting salicylaldehyde with 8-aminoquinoline. (XIII) can be made by reacting N,N-dimethylethylenediamine with salicylaldehyde. (XIV) can be made by reacting salicylaldehyde with 2-(N-2,6-diisoprpopylphenylimino)ethylamine. (XI) may be made by reacting 1,1,1-trifluoro-2,5-pentanedione with 2-aminomethylpyridine. (XVIII) may be made by reacting salicylaldehyde with 2-aminomethylthiophene. (XIX) may be made by reacting salicylaldehyde with 2-aminomethylfuran. (XX) may be made by reacting 1,1,1-trifluoro-2,5-pentanedione with 2-aminomethylfuran.

(I), the anion of the above conjugate acids, can be prepared by reaction of the conjugate acid with a strong base, such as an alkali metal hydride, an alkali metal alkoxide or a lithium disilylamide. It is preferred at this point that the cation to this anion is an alkali metal cation, such as lithium, sodium and potassium. (I) may isolated as a salt and then used to form the transition metal compound, or may be formed and used in situ to produce the transition metal compound. The transition metal compound of (I) may be prepared by reacting (I) with an appropriate compound of the transition metal. Especially for early transition metals such as Zr and Ti, the transition metal compound may be a halide such as $TiCl_4$ or $ZrCl_4$, in which case the ligands other than (I) attached to the metal will be halide such as chloride. Especially for late transition metal other types of compounds may be used. For example to make nickel complexes one may use:

$(Ph_3P)_2Ni(Ph)(Cl)$ which gives (IV) in which $L^1$ is Ph, and $L^2$ is $Ph_3P$;

$(TMEDA)_2Ni(Ph)(Cl)$ in the presence of a "trapping ligand" $L^2$ such as pyridine, which gives (IV) for instance in which $L^1$ is Ph, and $L^2$ is pyridine;

$(Ph_3P)_2NiCl_2$ which gives (IV) in which $L^1$ is Cl, and $L^2$ is $Ph_3P$; and/or $[(allyl)Ni(X)]_2$ which gives (IV) in which $L^1$ and $L^2$ taken together are π-allyl.

Methods of synthesis of these types of complexes may also be found in previously incorporated U.S. Pat. No. 6,060,569, WO9830609 and WO9842664, and in R. H. Grubbs., et al., *Organometallics*, vol. 17, p. 3149 (1988). If (V) is not already equivalent to (IV), it may be converted to (IV) before or during the polymerization process by reaction with other appropriate compounds (such as cocatalysts).

In some of the structures written herein, such as (IV) and (V), it is not meant that (I) is a tridentate ligand, although it may be. The structures are written as they are for convenience, and to show that the anionic ligands (I) could be tridentate, but it may be only bidentate or even monodentate. Although it is believed in theory the ligands can be tridentate, Applicants do not wish to be bound by this theory.

As implied above, (I) will normally be associated with a positively charged species, such as a cation. This may be a transition metal cation (as in (IV)), or may be another cation such as an alkali metal cation.

In (IV) useful groups $L^1$ include halide (especially chloride), hydrocarbyl and substituted hydrocarbyl especially phenyl and alkyl and particularly phenyl, methyl, hydride and acyl. Useful groups for $L^2$ include phosphine such as triphenylphosphine, nitrile such as acetonitrile, ethers such as ethyl ether, pyridine, and tertiary alkylamines such as TMEDA (N,N,N',N'-tetramethyl-1,2-ethylenediamine). Alternatively $L^1$ and $L^2$ taken together may be a π-allyl or π-benzyl group such as

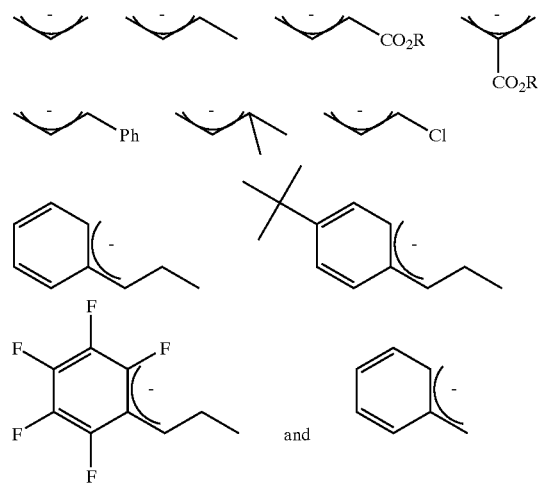

wherein R is hydrocarbyl, and π-allyl and π-benzyl groups are preferred.

In another variation, $L^3$ and $L^4$ taken together may be a β-diketonate ligand. If this ligand is present in (V), it may be converted to (IV) by use of a suitable alkylating agent such as an alkylaluminum compound, Grignard reagent, or alkyllithium compound.

In (IV) when ethylene may insert between $L^1$ and the transition metal atom, and $L^2$ is an empty coordination site or is a ligand which may be displaced by ethylene, or $L^1$ and $L^2$ taken together are a bidentate monoanionic ligand into which ethylene may be inserted between that ligand and the transition metal atom, (IV) may by itself catalyze the polymerization of an olefin. Examples of $L^1$ which form bonds with the transition metal into which ethylene may insert are hydrocarbyl and substituted hydrocarbyl, especially phenyl and alkyl, and particularly methyl, hydride and acyl. Ligands $L^2$ which ethylene may displace include phosphine such as triphenylphosphine, nitrile such as acetonitrile, ether such as ethyl ether, pyridine and tertiary alkylamines such as TMEDA. Ligands in which $L^1$ and $L^2$ taken together are a bidentate monoanionic ligand into which ethylene may insert between that ligand and the transition metal atom include π-allyl- or π-benzyl-type ligands (in this instance, sometimes it may be necessary to add a neutral Lewis acid cocatalyst such as triphenylborane to initiate the polymerization, see for instance previously incorporated WO9830609). For a summary of which ligands ethylene may insert into (between the ligand and transition metal atom) see, for instance, J. P. Collman, et al., *Principles and Applications of Organotransition Metal Chemistry,* University Science Book, Mill Valley, Calif., 1987, included herein by reference. If for instance $L^1$ is not a ligand into which ethylene may insert between it an the transition metal atom, it may be possible to add a cocatalyst which may convert $L^1$ into a ligand which will undergo such an insertion. Thus if $L^1$ is halo such as chloride or bromide, or carboxylate, it may be converted to hydrocarbyl such as alkyl by use of a suitable alkylating agent such as an alkylaluminum compound, a Grignard reagent or an alkyllithium compound. It may be converted to hydride by used of a compound such as sodium borohydride.

In (V) in one preferred form at least one of $L^3$ is a ligand into which ethylene may insert between $L^3$ and the transition metal atom, and $L^4$, is an empty coordination site or a ligand which may be displaced by ethylene. In another preferred for of (V) each of $L^3$ is a ligand into which ethylene may not insert between that ligand and the transition metal atom, such as halide, especially chloride, and carboxylate.

Generally a cocatalyst (sometimes also called an activator) which is an alkylating or hydriding agent is also present in the olefin polymerization. A preferred cocatalyst is an alkylaluminum compound, examples of which include trialkylaluminum compounds such as trimethylaluminum, triethylaluminum and tri-i-butylaluminum; alkyl aluminum halides such as diethylaluminum chloride and ethylaluminum chloride; and aluminoxanes such as methylaluminoxane. More than one such cocatalyst may be used in combination.

In (IV) and other transition metal complexes preferred metals are Pd, Co, Fe, Cr, V, Ti, Zr and Hf. More preferred are Ti, Zr, Pd and Ni, and Ni is especially preferred. Generally speaking early transition metal complexes such as Ti and Zr produce polymers with the "expected" number and length of branches (see previously incorporated U.S. Pat. No. 5,880,241 for an explanation of "expected" branching). For example homopolyethylene will have essentially no branching (after correcting for end groups), while poly(1-hexene) will have an n-butyl branch every other carbon atom (on average) of the main polymer chain. Polyolefins made with late transition metal complexes such as Ni or Pd will generally have the "wrong" number and branch lengths in the polyolefin. For example, homopolyethylene will often have branches of methyl and longer.

A preferred olefin is ethylene, and when olefins other than ethylene are polymerized, it is preferred that they be copolymers with ethylene. In other preferred olefins n is 1 to 20, and/or G is hydrogen, and/or G is —$CO_2R^{16}$ wherein $R^{16}$ is hydrocarbyl or substituted hydrocarbyl, especially alkyl.

In the polymerization processes herein, the temperature at which the polymerization is carried out is about −100° C. to about +200° C., preferably about −60° C. to about 150° C., more preferably about −20° C. to about 100° C. The pressure of the olefin (if it is a gas) at which the polymerization is carried out is not critical, atmospheric pressure to about 275 MPa being a suitable range.

The polymerization processes herein may be run in the presence of various liquids, particularly aprotic organic liquids. The catalyst system, monomer(s) and/or polymer may be soluble or insoluble in these liquids, but obviously these liquids should not prevent the polymerization from occurring. Suitable liquids include alkanes, cycloalkanes, selected halogenated hydrocarbons and aromatic hydrocarbons. Specific useful solvents include hexane, toluene, benzene methylene chloride, and 1,2,4-trichlorobenzene.

The olefin polymerizations herein may also initially be carried out in the "solid state" by, for instance, supporting the transition metal compound on a substrate such as silica or alumina, activating it if necessary with one or more cocatalysts and contacting it with the olefin(s). Alternatively, the support may first be contacted (reacted) with one or more cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle.

In all of the polymerization processes described herein oligomers and polymers of the various olefins are made. They may range in molecular weight from oligomeric POs (polyolefins), to lower molecular weight oils and waxes, to higher molecular weight POs. One preferred product is a polymer with a degree of polymerization (DP) of about 10 or more, preferably about 40 or more. By "DP" is meant the average number of repeat (monomer) units in a polymer molecule.

Depending on their properties, the polymer made by the processes described herein are useful in many ways. For instance if they are thermoplastics, they may be used as molding resins, for extrusion, films, etc. If they are elastomeric, they may be used as elastomers. If they contain functionalized monomers such as acrylate esters, they are useful for other purposes, see for instance previously incorporated U.S. Pat. No. 5,880,241.

Depending on the process conditions used and the polymerization catalyst system chosen, polymers, even those made from the same monomer(s) may have varying properties. Some of the properties that may change are molecular weight and molecular weight distribution, crystallinity, melting point and glass transition temperature. Except for molecular weight and molecular weight distribution, branching can affect all the other properties mentioned, and branching may be varied (using the same nickel compound) using methods described in previously incorporated U.S. Pat. No. 5,880,241.

It is known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers that inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. Monomers useful with these catalysts are those described (and also preferred) above. A second active polymerization catalyst (and optionally one or more others) is used in conjunction with the first active polymerization catalyst. The second active polymerization catalyst may be another late transition metal catalyst, for example as described in previously incorporated WO9830609, U.S. Pat. No. 5,880,241, U.S. Pat. No. 5,714,556 and U.S. Pat. No. 6,060,569, as well as U.S. Pat. No. 5,955,555, WO99/10391, WO97/38024, WO97/48735, WO98/38228, WO99/46302 and WO99/50318, which are also incorporated by reference herein for all purposes as if fully set forth.

Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem.*, Int. Ed. Engl., vol. 34, p. 1143–1170 (1995), EP-A-0416815 and U.S. Pat. No. 5,198,401 for information about metallocene-type catalysts, and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (the monomer(s) polymerized by the first active polymerization catalyst) and second olefin(s) [the monomer(s) polymerized by the second active polymerization catalyst] are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process them (co)polymerizes this olefin, either by itself or preferably with at least one other olefin, preferably ethylene, to form a branched polyolefin. Preparation of the oligomer (which is sometimes called an α-olefin) by a second active polymerization-type of catalyst can be found in previously incorporated U.S. Pat. No. 5,880,241 and WO99/02472 (included by reference).

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this process may vary in molecular weight and/or molecular weight distribution and/or melting point and/or level of crystallinity, and/or glass transition temperature and/or other factors. The polymers produced are useful as molding and extrusion resins and in films as for packaging. They may have advantages such as improved melt processing, toughness and improved low temperature properties.

Catalyst components which include transition metal complexes of (I), with or without other materials such as one or more cocatalysts and/or other polymerization catalysts are also disclosed herein. For example, such a catalyst component could include the transition metal complex supported on a support such as alumina, silica, a polymer, magnesium chloride, sodium chloride, etc., with or without other components being present. It may simply be a solution of the transition metal complex, or a slurry of the transition metal complex in a liquid, with or without a support being present.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. When liquid monomers (olefins) are present, one may need to experiment briefly to find the relative amounts of liquid monomers and hydrogen (as a gas). If both the hydrogen and monomer(s) are gaseous, their relative concentrations may be regulated by their partial pressures.

In the Examples, all pressures are gauge pressures. Branching was determined by $^1$H NMR, taking the total of the methyl carbon atoms as the number of branches. Branching is uncorrected for end groups. Some of the transition metal complexes may have one or molecules of THF coordinated per molecule of complex. In the examples the group "(A)" is the π-allyl group (XVIII)

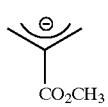

(XVIII)

The following abbreviations are used:

ΔH—heat of fusion

MI—melt index (2160 g, at 190° C.)

MMAO—modified methylaluminoxane (1.7 M in hexane) from Akzo Chemicals, Inc.

Mn—number average molecular weight

Mw—weight average molecular weight

PMAO-IP—Improved processing MMAO (4.5 M in toluene) from Akzo Chemicals, Inc.

PE—polyethylene

RT—room temperature

THF—tetrahydrofuran

Tm—melting point

EXAMPLE 1

Synthesis of (XVI)

A sample of 2.1809 g (9.30 mmol) of 3,5-di-t-butylsalicylaldehyde and 1.0064 g (9.3 mmol) of 2-aminomethylpyridine were placed in about 20 mL of methanol in a 100 mL flask and 3 drops of formic acid were added at RT. Since no precipitate formed, the methanol was removed and ether and sodium sulfate were added to the residue. The yellow solution was filtered through Celite® plug on a frit. After removal of the solvent, a yellow solid (2.5508 g, 7.86 mmol) product was obtained in 85% yield. $^1$H NMR (CDCl$_3$): 1.24 (s, 9H, CH$_3$), 1.34 (s, 9H, CH$_3$), 4.82 (s, 2H, CH$_2$), 7.11 (d, 1H, Ar—H), 7.14 (t, 1H, Py—H), 7.27 (d, 1H, Py—H), 7.3 (d, 1H, Ar—H), 7.63 (t, 1H, Py—H), 8.48 (s and s, 2H, Py—H and C—H).

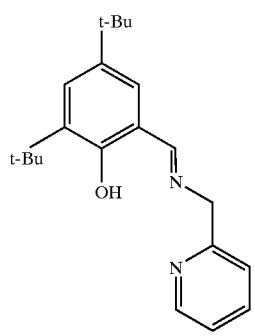

(XVI)

EXAMPLE 2

Synthesis of (XVII)

A sample of 4.445 g (0.021 mol) of 3,5-di-nitrosalicylaldehyde and 2.7194 g (0.025 mol) of 2-aminomethylpyridine were placed in about 80 mL of methanol in a 250 mL flask and 5 drops of formic acid was added at RT. A yellow precipitate formed immediately. The reaction mixture was stirred overnight and filtered to collect the yellow solid which then was dissolved in THF and dried with sodium sulfate. After removal of the solvent, a yellow solid (5.3088 g, 0.018 mol) was obtained in 84% yield. $^1$H NMR (CD$_2$Cl$_2$): 4.94 (s, 2H, CH$_2$), 7.22 (t, 1H, Py—H), 7.28 (d, 1H, Py—H ), 7.66 (t, 1H, Py—H), 8.44 (d, 1H, Ar—H), 8.52 (d, 1H, Ar—H), 8.60 (s, 1H, C—H), 8.78 (d, 1H, Py—H).

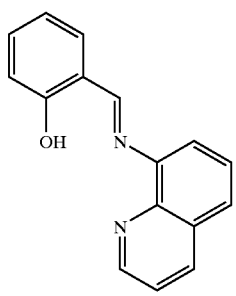

(XVII)

EXAMPLE 3

Synthesis of the Sodium salt of (XVII)

In a dry box, 0.0683 g (2.85 mmol) of sodium hydride was slowly added to a suspension of (XVII) (0.7818 g, 2.587 mmol) in 20 mL of THF. An orange precipitate formed while hydrogen gas was released. The reaction mixture was stirred overnight and filtered to collect the orange solid which then was rinsed with THF and pentane and dried under vacuo. An orange powder (0.6401 g, 1.97 mmol) was obtained in 76% yield.

EXAMPLE 4

Synthesis of the Sodium salt of (XVI)

In a dry box, 0.0966 g (4.025 mmol) of sodium hydride was slowly added to a solution of (XVI) (1.1873 g, 3.66 mmol) in 50 mL of THF. The reaction mixture was stirred overnight and filtered through a Celite® plug on a frit. The solvent was removed and the residue was rinsed with pentane and dried under vacuo. A pale yellow solid (1.1593 g, 3.35 mmol) was obtained in 91% yield. $^1$H NMR ($C_6D_6$): 1.28 (m, THF—$CH_2$), 1.28 (s, 9H, $CH_3$), 1.50 (s, 9H, $CH_3$), 3.42 (m, THF—$CH_2$), 4.25 (s, 2H, $CH_2$), 6.30 (br, 1H, Ar—H), 6.42 (br, 1H, Py—H), 6.78 (br, 1H, Py—H), 6.90 (br, 1H, Ar—H), 7.46 (br, 1H, Py—H), 7.68 (br, 1H, Py—H), 7.92 (br, 1H, C—H).

EXAMPLE 5

Synthesis of (XVII)•Ni(A)

In a dry box, 0.0804 g (0.169 mmol) of π-[$H_2CC(CO_2Me$)$CH_2$]Ni($\mu$—$Br_2$) (see World Patent Application 9830609) and the product of Example 3 (0.1097 g, 0.338 mmol) were mixed in 20 mL of THF and stirred for one h. The reaction mixture was filtered to collect the brown solid which then was rinsed with THF and pentane and dried under vacuo. An orange powder (0.1427 9, 0.31 mmol) was obtained in 92% yield.

EXAMPLE 6

Synthesis of (XVI)•Ni(A)

In a dry box, 0.0995 g (0.209 mmol) of methyl methacrylate nickel bromide dimer and the product of Example 4 (0.1450 g, 0.418 mmol) were mixed in 20 mL of THF and stirred for one h. The solvent was removed under vacuo. The dark brown residue was dissolved in methylene chloride and the solution was filtered through Celite® plug on a frit. After removal of the solvent, the brown solid was rinsed with pentane and dried under vacuo. Product (0.1203 g, 0.25 mmol) was obtained in 60% yield. The $^1$H NMR was complex.

EXAMPLE 7

Synthesis of (XVII)•$TiCl_3$

In a dry-box, a suspension of 0.1197 g (0.3695 mmol) of the product of Example 3 (0.1097 g, 0.338 mmol) in 20 mL of a mixture of toluene and THF (1:1) was added dropwise to a pre-cooled solution of $TiCl_4$(THF)$_2$ (0.1234 g, 0.3695 mmol) in 20 mL of toluene at −30° C. The brown reaction mixture was stirred 3 d and filtered to collect the solid, which was then rinsed with THF and pentane and dried under vacuo. A light brown powder (0.1109 g, 0.24 mmol) was obtained in 66% yield.

EXAMPLE 8

Synthesis of (XVI)•$TiCl_3$

In a dry-box, a solution containing a sample of 0.2135 g (0.616 mmol) of the product of Example 4 in 20 mL of toluene was added dropwise to a pre-cooled solution of $TiCl_4$(THF)$_2$ (0.2058 9, 0.616 mmol) in 20 mL of toluene at −30° C. The red reaction mixture was stirred 3 d and filtered through a Celite® plug on top of a frit. Removed the solvent, rinsed the residue with pentane and dried under vacuo. An orange powder (0.2624 g, 0.55 mmol) was obtained in 89% yield. $^1$H NMR ($CD_2Cl_2$): 1.41 (s, 9H, $CH_3$), 1.60 (s, 9H, $CH_3$), 5.54 (s, 2H, $CH_2$), 7.48 (d, 1H, Ar-H), 7.57 (d, 1H, Py—H), 7.64 (t, 1H, Py—H), 7.78 (d, 1H, Ar—H), 8.08 (t, 1H, Py—H), 8.45 (s, 1H, C—H), 9.46 (d, 1H, Py—H).

EXAMPLE 9

Synthesis of (XVI)•$ZrCl_3$

In a dry-box, a solution of 0.1920 g (0.554 mmol) of the product of Example 4 in 20 mL of toluene was added dropwise to a pre-cooled solution of $ZrCl_4$(THF)$_2$ (0.2091 g, 0.554 mmol) in 20 mL of toluene at −30° C. The yellow reaction mixture was stirred 3 d and filtered through a Celite® plug on top of a frit. Removed the solvent, rinsed the residue with pentane and dried under vacuo. A yellow powder (0.2528 g, 0.485 mmol) was obtained in 88% yield. $^1$H NMR ($CD_2Cl_2$) 1.27 (s, 9H, $CH_3$), 1.44 (s, 9H, $CH_3$), 1.73 (br, CH2, THF), 3.60 (br, CH2, THF), 5.38 (s, 2H, $CH_2$), 7.30 (d, 1H, Ar—H), 7.53 (m, 2H, Py—H), 7.65 (d, 1H, Ar—H), 8.02 (t, 1H, Py—H), 8.40 (s, 1H, C—H), 9.05 (d, 1H, Py—H).

EXAMPLE 10

Synthesis of (XVI)•CoCl

In a drybox, a solution containing a sample of 0.3103 g (0.8957 mmol) of the product of Example 4 in 20 mL of THF was added dropwise to a pre-cooled suspension of $CoCl_2$ (0.1163 g, 0.8957 mmol) in 10 mL of toluene at −30° C. The red brown reaction mixture was stirred overnight. Removed the solvent, extracted the residue with methylene chloride and dried under vacuo. A yellowish green powder (0.3103 g, 0.743 mmol) was obtained in 83% yield. $_1$H NMR ($CD_2Cl_2$) very broad due to paramagnetism.

EXAMPLE 11

Synthesis of (XVI)•$CrCl_2$

In a dry-box, a solution of 0.1248 g (0.36 mmol) of the product of Example 4 in 20 mL of toluene was added dropwise to a pre-cooled solution of $CrCl_3$(THF)$_3$ (0.1350 g, 0.36 mmol) in 20 mL of toluene and 2 mL of THF at −30° C. The brown reaction mixture was stirred 3 d and filtered through a Celite® plug on top of a frit. After removing the solvent, the residue was rinsed with pentane and dried under vacuo. A brown powder (0.112 g, 0.25 mmol) was obtained in 70% yield. $^1$H NMR ($CD_2Cl_2$): very broad due to paramagnetism.

EXAMPLES 12–22

Polymerization of Ethylene

In a drybox, 0.02 mmol of the transition metal compound (catalyst) was placed in a glass vial and dissolved in 5 mL of 1,2,4-trichlorobenzene. The vial was cooled to −30° C. in the drybox freezer. PMAO was added to the vial on top of the frozen solution, then the vial was capped, sealed and placed into a shaker tube which was then shaken mechanically under 3.45 MPa of ethylene in a shaker apparatus outside the dry box for about 18 h. The reaction mixture was slowly poured to a 100 mL of methanol solution of concentrated HCl (10% volume). The mixture was stirred overnight and filtered. The polymer was collected on a frit, washed with acetone and dried in vacuo.

If a cocatalyst was triarylborane, catalyst and cocatalyst were placed in the reaction vial and cooled at −30° C., then 1,2,4-trichlorobenzene was added.

Results of the polymerization are given in Table 1.

TABLE 1

| Ex. | Catalyst | Cocatalyst (equiv.) | PE (g) | Productivity (mol PE/mol Catalyst) | MI | $M_W$ | Tm (° C.), ΔH (J/g) | Me/1000 $CH_2$ |
|---|---|---|---|---|---|---|---|---|
| 12 | (XVI) •Ni (A) | $BPh_3$ (20) | 0 | 0 | | | | |
| 13 | (XVI) •Ni (A) | $B(C_6F_5)_3$ (20) | 3.2882 | 5757 | 198 | 9694 bimodal | 43.98, —<br>115.41, 4.509 | 83.92 |
| 14 | (XVI) •Ni (A) | MMAO (300) | 1.2006 | 2000 | 56.4 | 53499 bimodal | 119.81, 30.8 | 108.26 |
| 15 | (XVII) •Ni (A) | $BPh_3$ (20) | 0 | 0 | | | | |
| 16 | (XVII) •Ni (A) | $B(C_6F_5)_3$ (20) | 1.076 | 1779 | 0.33 | 181632 very broad | 127.74, 204.8 | 19.5 |
| 17 | (XVII) •Ni (A) | MMAO (300) | 2.0038 | 3489 | 0.06 | 279468 bimodal | 126.26, 166.2 | 28.25 |
| 18 | (XVI) •CoCl | MMAO (300) | 0.2084 | 358 | | 30160 | 126.96, 63.81 | 72.45 |
| 19 | (XVI) •$TiCl_3$[a] | MMAO (500) | 8.4812 | $2.83 \times 10^4$ | 0 | insoluble | 133.98, 188.6 | 7.97 |
| 20 | (XVII) •$TiCl_3$[a] | MMAO (500) | 4.9081 | $1.66 \times 10^4$ | 0 | insoluble | 127.49, 198.3 | 7.6 |
| 21 | (XVI) •$CrCl_2$ | MMAO (500) | 0.0558 | 100 | | 49926 | 129.71, 226.7 | 21.22 |
| 22 | (XVI) •$ZrCl_3$ | MMAO (500) | 7.489 | $1.28 \times 10^4$ | 0 | insoluble | 135.49, 208.5 | 0 |

[a] 0.01 mmol catalyst.

EXAMPLES 23–25

Copolymerization of 1-Hexene and Ethylene

In a drybox, 0.005 mmol of the catalyst was placed in a glass vial and dissolved in 3 mL of 1,2,4-trichlorobenzene. The vial was cooled to −30 C in the drybox freezer. PMAO (500 equiv.) and 2 mL of 1-hexene then were added to the vial on top of the frozen solution, then the vial was capped, sealed and placed into a shaker tube which was then shaken mechanically in a shaker apparatus under 1.38 MPa ethylene for about 18 h. The reaction mixture was slowly poured to a 100 mL of methanol solution of concentrated HCl (10% volume). The mixture was stirred overnight and filtered. The polymer was collected on a frit, washed with acetone and dried in vacuo. The copolymer formed was high in molecular weight because in the melt index test there was no flow. Results of the polymerizations are given in Table 2.

TABLE 2

| Ex | Catalyst | Copolymer (g) | Productivity (kg polymer/mol Cat.) | Tm (° C.), ΔH (J/g) | Me/1000 $CH_2$ |
|---|---|---|---|---|---|
| 23 | (XVII) •$TiCl_3$ | 0.9151 | 42.9 | 120.27, 59.96 | 54.89 |
| 24 | (XVI) •$TiCl_3$ | 4.1818 | 951.3 | 114.84, 51.83 | 38.46 |
| 25 | (XVI) •$ZrCl_3$ | 3.0236 | 525.1 | 129.07, 116.0 | 14.94 |

EXAMPLE 26

Polymerization of Ethylene

In a drybox, 40 mL of toluene and 0.93 mL (4.29 mmol) of PMAO-IP were placed in a 100 mL Schlenk flask and stirred 3 min. Then 0.0041 g (0.0086 mmol)of (XVI)•$TiCl_3$ was added to the solution. The flask was sealed, removed from the drybox and attached to an ethylene Schlenk line. After pumping off the air and nitrogen and purging with ethylene, the reaction mixture was stirred 20 min under ethylene (34.5 kPa) and quenched with 50 mL of a methanol solution of concentrated HCl (10% volume). The polymer was collected on a frit, washed with methanol and acetone thoroughly and then, dried in vacuo overnight. A crystalline white polymer (1.0257 g) was obtained with $M_W$=387728, $M_W/M_n$=3.82; Me/1000$CH_2$ ($^1$H NMR in TCE-$d_2$)=0.0 and Tm=134.31, ΔH=165.0 J/g.

EXAMPLE 27

Copolymerization of 1-Hexene and Ethylene

In a drybox, 40 mL of toluene, 0.9 mL (4.05 mmol) of PMAO-IP and 5 mL of 1-hexene were placed in a 100 mL Schlenk flask and stirred 3 min. Then 0.0039 g (0.0082 mmol) of the (XVI)•$TiCl_3$ was added to the solution. The flask was sealed, removed from the drybox and attached to an ethylene Schlenk line. After pumping off the air and nitrogen and purging with ethylene, the reaction mixture was stirred 45 min under ethylene (34.5 kPa) and quenched with 50 mL of a methanol solution of concentrated HCl (10% volume). The polymer was collected on a frit, washed with methanol and acetone thoroughly, and then dried in vacuo overnight. A rubbery white polymer (1.705 g, 207.93 kg polymer/mol catalyst) was obtained with $M_W$=624577, $M_W/M_n$=3.02; Me/1000$CH_2$($^1$H NMR in TCE-$d_2$)=46.83 and $T_m$=76.95, ΔH=33.35 J/g.

What is claimed is:

1. A compound of the formula (V)

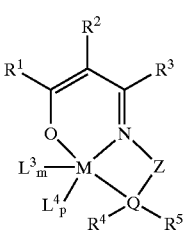

(V)

wherein:
$R^1$ is hydrocarbyl or substituted hydrocarbyl;
$R^2$ is hydrogen, hydrocarbyl or substituted hydrocarbyl;
with the proviso that $R^1$ and $R^2$ taken together may be ortho-arylene or substituted ortho-arylene;

R³ is hydrogen, hydrocarbyl, substituted hydrocarbyl or a functional group, provided that when R¹ and R² taken together are ortho-arylene or substituted ortho-arylene, R³ may form a fused ring system therewith;

R⁴ and R⁵ are each independently hydrogen, hydrocarbyl, or substituted hydrocarbyl, provided that R⁴ and R⁵ taken together may form a ring, and further provided that when Q is oxygen or sulfur R⁵ is not present; Q is nitrogen, oxygen, phosphorous or sulfur;

Z is a bridging group of the formula (II) or (III)

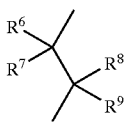
(II)

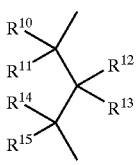
(III)

R⁶ is hydrogen, hydrocarbyl or substituted hydrocarbyl, or R³ and R⁶ together may form a ring;

R⁷ is hydrogen, hydrocarbyl or substituted hydrocarbyl, provided that R³, R⁶ and R⁷ together may form an aromatic ring, or R⁶ and R⁷ taken together may form a ring;

R⁸ is hydrogen, hydrocarbyl or substituted hydrocarbyl;

R⁹ is hydrogen, hydrocarbyl, substituted hydrocarbyl, or R⁴ and R⁹ taken together may be part of a double bond to an imino nitrogen atom, or R⁸ and R⁹ taken together may form a ring, or R⁴, R⁵, R⁸ and R⁹ taken together may form an aromatic ring, or R⁴ and R⁹ taken together may form a ring, or R⁴, R⁸ and R⁹ taken together may form a ring R¹⁰, R¹¹, R¹² and R¹³ are each independently hydrogen, hydrocarbyl or substituted hydrocarbyl, or R¹⁰, R¹¹, R¹² and R¹³ taken together are ortho-arylene;

R¹⁴ is hydrogen, hydrocarbyl or substituted hydrocarbyl;

R⁴ and R¹⁵ together are part of a double bond to an imino nitrogen atom;

M is selected from the group consisting of Ni, Pd, Fe, Cr, V, Ti, Zr and Hf;

m is an integer equal to the valence of M minus 1;

p is 0 or 1; and each L³ is independently a monodentate monoanionic ligand, and L⁴ is a monodentate neutral ligand or an empty coordination site, or an L³ and L⁴ taken together are a monoanionic bidentate ligand.

2. The compound as recited in claim 1, wherein the transition metal is Ni.

3. The compound as recited in claim 1, wherein Q is nitrogen; R¹ and R² taken together are o-arylene, Z is a group of the formula (II), and R⁴, R⁵, R⁸ and R⁹ taken together form an aromatic ring.

4. An olefin polymerization catalyst comprising a Ni, Pd, Fe, Cr, V, Ti, Zr or Hf complex of an anion of the formula (I)

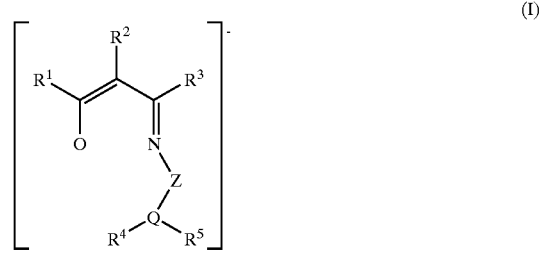
(I)

wherein:

R¹ is hydrocarbyl or substituted hydrocarbyl, and R² is hydrogen, hydrocarbyl or substituted hydrocarbyl, and provided that R¹ and R² taken together may be ortho-arylene or substituted ortho-arylene;

R³ is hydrogen, hydrocarbyl, substituted hydrocarbyl or a functional group, provided that when R¹ and R² taken together are ortho-arylene or substituted ortho-arylene, R³ may form a fused ring system therewith;

Q is nitrogen, oxygen, phosphorous or sulfur;

R⁴ and R⁵ are each independently hydrogen, hydrocarbyl, or substituted hydrocarbyl, provided that R⁴ and R⁵ taken together may form a ring, and further provided that when Q is oxygen or (sulfur R⁵ is not present;

Z is a bridging group of the formula (II) or (III)

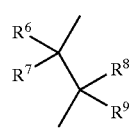
(II)

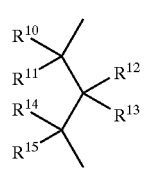
(III)

R⁶ is hydrogen, hydrocarbyl or substituted hydrocarbyl, provided that R³ and R⁶ together may form a ring;

R⁷ is hydrogen, hydrocarbyl or substituted hydrocarbyl, provided that R³, R⁶ and R⁷ together may form an aromatic ring or R⁶ and R⁷ taken together may form a ring;

R⁸ is hydrogen, hydrocarbyl or substituted hydrocarbyl;

R⁹ is hydrogen, hydrocarbyl or substituted hydrocarbyl, provided that R⁴ and R⁹ taken together may be part of a double bond to an imino nitrogen atom, or R⁸ and R⁹ taken together may form a ring, or R⁴, R⁵, R⁸ and R⁹ taken together may form an aromatic ring, or R⁴ and R⁹ taken together may form a ring, or R⁴, R⁸ and R⁹ taken together may form a ring, or R⁴, R⁵, R⁶, R⁷, R⁸, and R⁹ taken together may form a fused aromatic ring system;

R¹⁰, R¹¹, R¹² and R¹³ are each independently hydrogen, hydrocarbyl or substituted hydrocarbyl or R¹⁰, R¹¹, R¹² and R¹³ taken together are ortho-arylene;

R¹⁴ is hydrogen, hydrocarbyl or substituted hydrocarbyl;

R⁴ and R¹⁵ together are part of a double bond to an imino nitrogen atom.

5. The catalyst of claim 4 wherein said complex is a complex of Ti, Zr, Pd, or Ni.

6. The olefin polymerization catalyst as recited in claim 4, wherein Q is nitrogen; $R^1$ and $R^2$ taken together are o-arylene, Z is a group of the formula (II), and $R^4$, $R^5$, $R^8$ and $R^9$ taken together form an aromatic ring.

7. The olefin polymerization catalyst as recited in claim 4, further comprising a catalyst activator.

* * * * *